(12) United States Patent
Hsieh

(10) Patent No.: US 6,570,951 B1
(45) Date of Patent: May 27, 2003

(54) IMAGE SPACE COMPENSATION SCHEME FOR REDUCING ARTIFACTS

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/063,799

(22) Filed: May 14, 2002

(51) Int. Cl.$^7$ ............................................. A61B 6/03
(52) U.S. Cl. ........................... 378/4; 378/15; 378/901
(58) Field of Search ........................... 378/4, 8, 15, 901

(56) References Cited

U.S. PATENT DOCUMENTS

| | | | |
|---|---|---|---|
| 5,165,100 A | 11/1992 | Hsieh et al. ............... 382/6 |
| 5,225,980 A | 7/1993 | Hsieh et al. | |
| 5,818,896 A | 10/1998 | Hsieh ....................... 378/15 |
| 6,215,841 B1 | 4/2001 | Hsieh ....................... 378/8 |
| 6,493,419 B1 * | 12/2002 | Dinsmore ................. 378/65 |
| 2002/0118887 A1 * | 8/2002 | Gindele .................... 382/260 |

* cited by examiner

Primary Examiner—David V. Bruce
(74) Attorney, Agent, or Firm—Cantor Colburn LLP

(57) ABSTRACT

A method and system for reducing artifacts in an x-ray image generated by a computed tomography imaging system using an image space compensation scheme including obtaining reconstructed image data generated using an image reconstruction algorithm, determining a noise variation characteristic for the reconstruction algorithm, filtering the reconstructed image data so as to create smoothed image data and processing the smoothed image data and the reconstructed image data so as to create corrected image data. Also claimed is a medium encoded with a machine-readable computer program code for reducing artifacts in an x-ray image, the medium including instructions for causing controller to implement the aforementioned method.

29 Claims, 5 Drawing Sheets

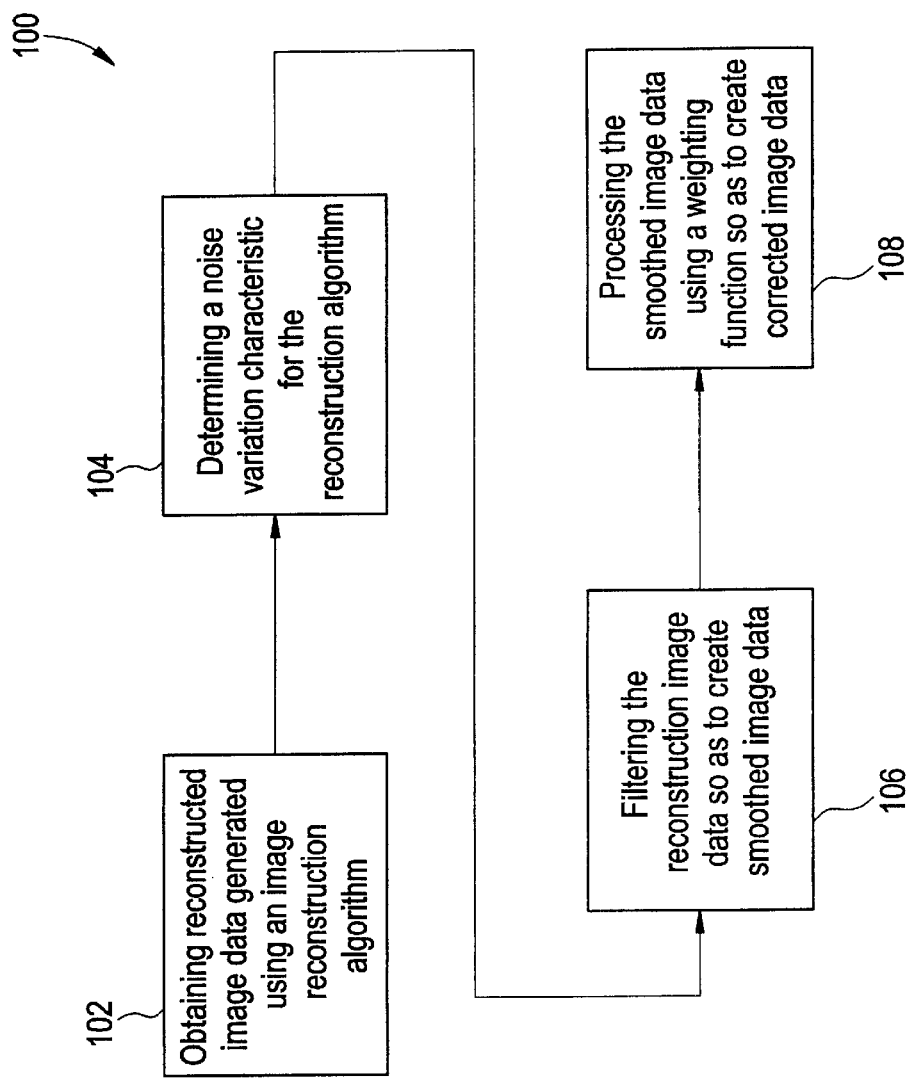

| | 8-slice 13.4:1 pitch | 8-slice 10.8:1 pitch | 8-slice 7:1 pitch | 8-slice 5:1 pitch | 4-slice 3:1 pitch | 4-slice 6:1 pitch |
|---|---|---|---|---|---|---|
| $\alpha$ | 0.65 | 0.75 | 0.0 | 0.3 | 0.0 | 0.65 |

IMAGE SPACE COMPENSATION SCHEME FOR REDUCING ARTIFACTS

BACKGROUND OF INVENTION

This invention relates generally to a method and system for reducing artifacts in an image and more particularly to a method and system using an image space compensation scheme for reducing artifacts in an X-ray image generated by a Computed Tomography (CT) imaging system.

In CT imaging systems, an x-ray source projects a fan-shaped beam that is collimated to lie within an X-Y plane, generally referred to as an "imaging plane", of a Cartesian coordinate system toward an array of radiation detectors, wherein each radiation detector includes a detector element disposed within the CT system so as to receive this fan-shaped beam. An object, such as a patient, is disposed between the x-ray source and the radiation detector array so as to lie within the imaging plane and so as to be subjected to the x-ray beam, which passes through the object. As the x-ray beam passes through the object, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam intensity at the detector element location. These electrical signals are referred to as x-ray attenuation measurements or x-ray images.

Moreover, the x-ray source and the detector array may be rotated, with a gantry within the imaging plane, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to a two-dimensional slice taken through the object. In CT systems that employ a single detector array, the slice thickness is controlled and determined by the width of the collimator, while in CT systems that employ a multiple detector array, the slice thickness is controlled and determined by summing the contributions of a plurality of detector sub-units and by physically moving the collimator to the outer edges of each slice.

With the introduction of multi-slice computed tomography (CT), nearly isotropic spatial resolution may be obtained using helical scans. In order to reduce the number of images necessary for each study, more and more radiologists utilize 3-D visualization tools to perform diagnosis. One of the more popular visualization tools employs a technique known as maximum intensity projection (MIP) processing.

In MIP processing the direction of an imaginary ray forward projection is determined and a maximum pixel value along each forward projection ray is identified. The projection value for each projection ray is then assigned to this maximum pixel value, resulting in the production of 2-D projection data from a 3-D image volume. In addition, a similar but slightly different visualization technique is called volume rendering (VR). In VR, an imaginary ray forward projection is also produce, but unlike the MIP process the projection value is determined based on the integrated opacity along the projection ray path. The opacity is obtained based on a mapping function that maps the image intensity to certain opacity values.

However, because of the interaction between the helical weighting and the scaling in the fan-beam back-projection process, the noise in the reconstructed image is both non-uniform and non-stationary and thus no longer homogenous. In addition, because the noise variation follows the x-ray tube position a periodic intensity modulation in the MIP image, known as the Venetian blind artifact or zebra artifact, is created. Thus, as a result of the inhomogeneous nature of the noise distribution in 3D or MIP images bias, in the form of bright and dark bands or spiral pattern artifacts, is produced. For certain weighting functions, the noise difference can be more than a factor of two even for the reconstruction of a homogeneous object.

Unfortunately, two obstacles currently exist with present methods of removing or reducing these artifacts from reconstructed images. First, these methods require a great deal of time and processing power in order to reconstruct the image. Second, these methods are unable to handle images having large amounts of artifacts. Therefore, there is a need for an algorithm that facilitates the reduction of artifacts, wherein the algorithm does not significantly increase the image reconstruction processing time.

SUMMARY OF INVENTION

The above discussed and other drawbacks and deficiencies are overcome or alleviated by a method for reducing artifacts in an x-ray image generated by a computed tomography imaging system using an image space compensation scheme comprising: obtaining reconstructed image data generated using an image reconstruction algorithm; determining a noise variation characteristic for the reconstruction algorithm; filtering the reconstructed image data so as to create smoothed image data and processing the smoothed image data and the reconstructed image data so as to create corrected image data.

A medium encoded with a machine-readable computer program code for reducing artifacts in an x-ray image generated by a computed tomography imaging system using an image space compensation scheme, the medium including instructions for causing a controller to implement a method comprising: obtaining reconstructed image data generated using an image reconstruction algorithm; determining a noise variation characteristic for the reconstruction algorithm; filtering the reconstructed image data so as to create smoothed image data; and processing the smoothed image data and the reconstructed image data so as to create corrected image data.

A method for reducing artifacts in an image comprising: obtaining an imaging system and an object to be scanned; operating the imaging system so as to create projection data responsive to the object; examining the projection data so as to determine if the projection data should be processed; and processing the projection data using an image space compensation scheme wherein the compensation scheme, obtains reconstructed image data generated using an image reconstruction algorithm; determines a noise variation characteristic for the reconstruction algorithm; filters the reconstructed image data so as to create smoothed image data; and processes the smoothed image data and the reconstructed image data so as to create corrected image data.

A system for reducing artifacts in an x-ray image comprising: a gantry having an x-ray source and a radiation detector array, wherein the gantry defines an object cavity and wherein the x-ray source and the radiation detector array are rotatingly associated with the gantry so as to be separated by the object cavity; a object support structure movingly associated with the gantry so as to allow communication with the object cavity; and a processing device having an image space compensation scheme, wherein the compensation scheme, obtains reconstructed image data generated using an image reconstruction algorithm; determines a noise variation characteristic for the reconstruction algorithm; filters the reconstructed image data so as to create smoothed image data; and processes the smoothed image data and the reconstructed image data so as to create corrected image data.

A system for reducing artifacts in an image using an image space compensation scheme comprising: an imaging system; an object disposed so as to be communicated with the imaging system, wherein the imaging system generates projection data responsive to the object; and a processing device, wherein the processing device, obtains reconstructed image data generated using an image reconstruction algorithm; determines a noise variation characteristic for the reconstruction algorithm; filters the reconstructed image data so as to create smoothed image data; and processes the smoothed image data and the reconstructed image data so as to create corrected image data.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures:

FIG. 3 is a flow diagram describing a method for reducing artifacts in an X-ray image, in accordance with an exemplary embodiment;

DETAILED DESCRIPTION

In accordance with an exemplary embodiment, while a method and system for reducing artifacts in an x-ray image generated by an imaging system using an image space compensation scheme is described and discussed hereinbelow with reference to a computed tomography (CT) imaging system, it should be understood that the method and system of the invention may be applied to other imaging systems, such as Magnetic Resonance Imaging (MRI) and/or Positron Emission Tomography (PET).

Figure 1:
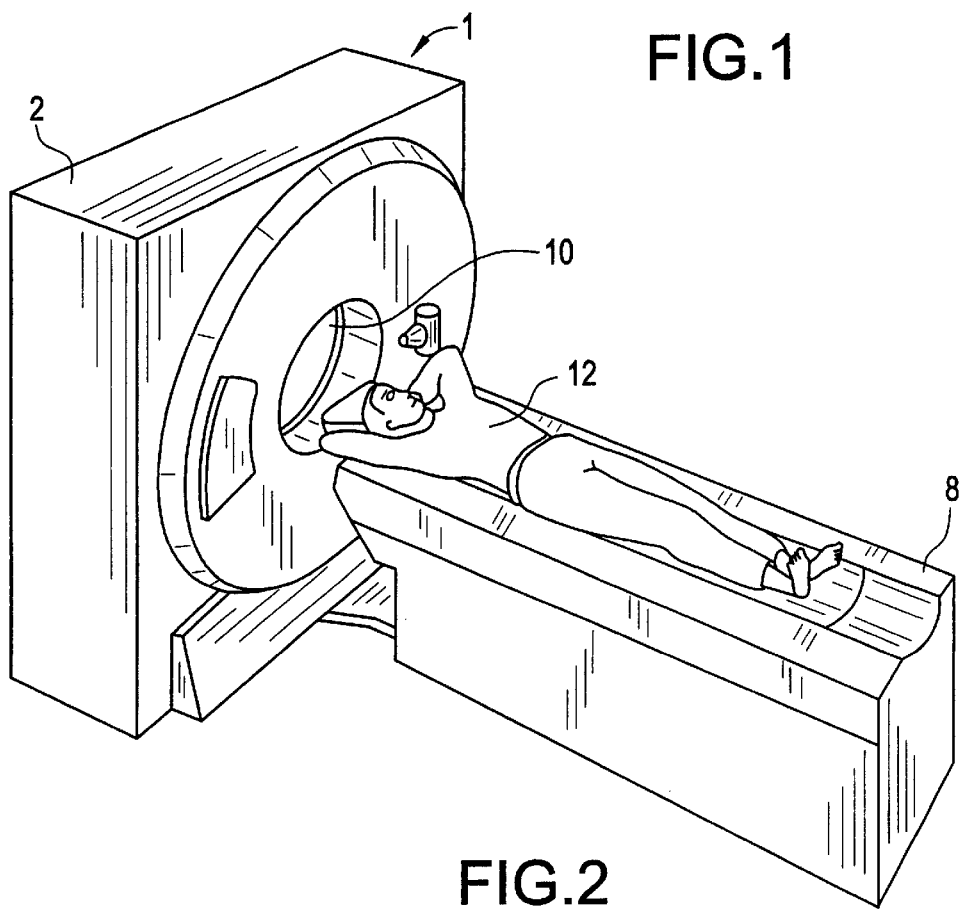
FIG. 1 is a perspective view of a CT imaging system and a patient disposed for imaging.
Figure 2:
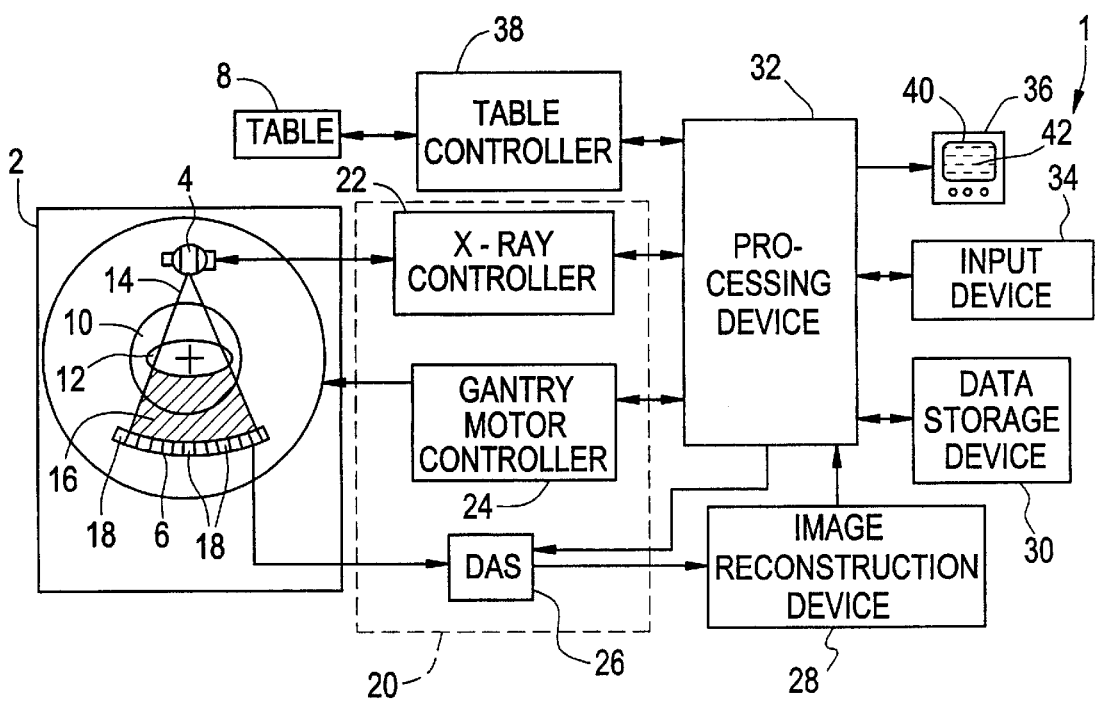
FIG. 2 is a block schematic diagram of a CT imaging system.

Referring to FIG. 1 and FIG. 2, a representative CT imaging system 1 is shown and includes a gantry 2 having an x-ray source 4, a radiation detector array 6, a patient support structure 8 and a object cavity 10, wherein x-ray source 4 and radiation detector array 6 are opposingly disposed so as to be separated by object cavity 10. An object, such as a patient 12, is dispose upon patient support structure 8 which is then disposed within object cavity 10. X-ray source 4 projects an x-ray beam 14 toward radiation detector array 6 so as to pass through patient 12. X-ray beam 6 is then collimated by a collimate (not shown) so as to lie within an X-Y plane of a Cartesian coordinate system referred to as an "imaging plane". After passing through and becoming attenuated by patient 12, attenuated x-ray beam 16 is received by radiation detector array 6. Radiation detector array 6 includes a plurality of detector elements 18 wherein each of said detector elements 18 receives attenuated x-ray beam 16 and produces an electrical signal responsive to the intensity of attenuated x-ray beam 16.

In addition, x-ray source 4 and radiation detector array 6 are rotatingly disposed relative to gantry 2 and patient support structure 8, so as to allow x-ray source 4 and radiation detector array 6 to rotate around patient support structure 8 when patient support structure 8 is disposed within object cavity 10. X-ray projection data is obtained by rotating x-ray source 4 and radiation detector array 6 around patient 10 during a scan. X-ray source 4 and radiation detector array 6 are preferably communicated with a control mechanism 20 associated with CT imaging system 1. Control mechanism 20 controls the rotation and operation of x-ray source 4 and radiation detector array 6.

Control mechanism 20 includes an x-ray controller 22 communicated with x-ray source 4, a gantry motor controller 24, and a data acquisition system (DAS) 26 communicated with radiation detector array 6, wherein x-ray controller 22 provides power and timing signals to x-ray source 4, gantry motor controller 24 controls the rotational speed and angular position of x-ray source 4 and radiation detector array 6 and DAS 26 receives the electrical signal data produced by detector elements 18 and converts this data into digital signals for subsequent processing. CT imaging system 1 also includes an image reconstruction device 28, a data storage device 30 and a processing device 32, wherein processing device 32 is communicated with image reconstruction device 28, gantry motor controller 24, x-ray controller 22, data storage device 30, an input device 34 and an output device 36. Moreover, CT imaging system 1 also includes a table controller 38 communicated with processing device 32 and patient support structure 8, so as to control the position of patient support structure 8 relative to object cavity 10.

Patient 12 is preferably disposed on patient support structure 8, which is then positioned by an operator via processing device 32 so as to be disposed within object cavity 10. Gantry motor controller 24 is operated via processing device 32 so as to cause x-ray source 4 and radiation detector array 6 to rotate relative to patient 12. X-ray controller 22 is operated via processing device 32 so as to cause x-ray source 4 to emit and project a collimated x-ray beam 14 toward radiation detector array 6 and hence toward patient 12. X-ray beam 14 passes through patient 12 so as to create an attenuated x-ray beam 16, which is received by radiation detector array 6.

Detector elements 18 receive attenuated x-ray beam 16, produces electrical signal data responsive to the intensity of attenuated x-ray beam 16 and communicates this electrical signal data to DAS 26. DAS 26 then converts this electrical signal data to digital signals and communicates both the digital signals and the electrical signal data to image reconstruction device 28, which performs high-speed image reconstruction. This information is then communicated to processing device 32, which stores the image in data storage device 30 and displays the digital signal as an image via output device 36.

Figure 4A:
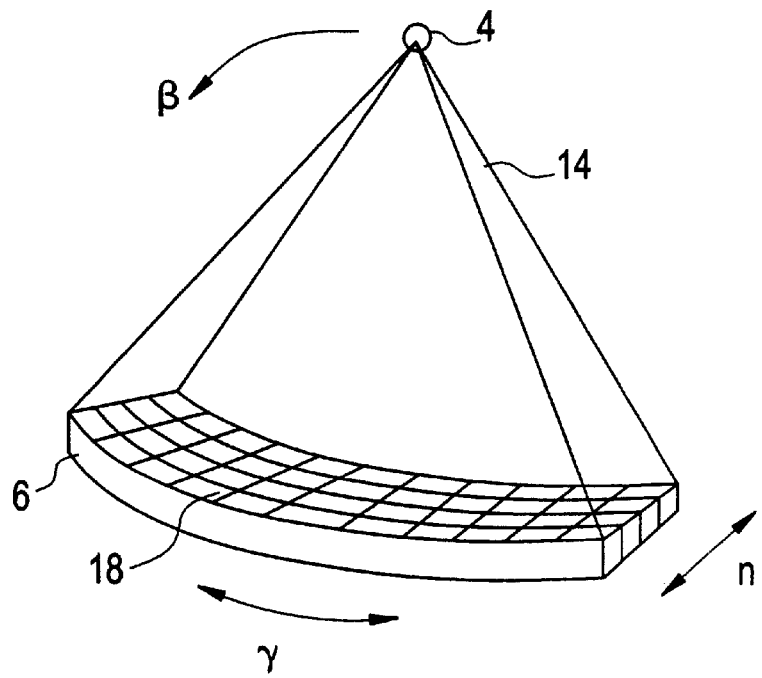
FIG. 4A is an example of an arrangement of an x-ray source, an x-ray beam and a radiation detector array.
Figure 4B:
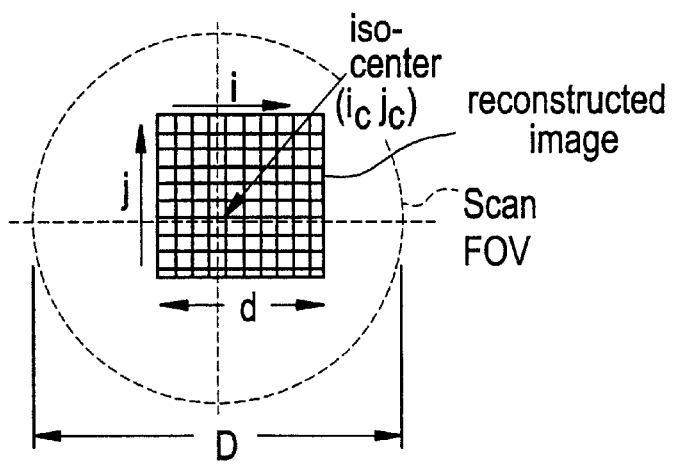
FIG. 4B shows the iso-center of a reconstructed image within an entire CT scan field of view.

Referring to FIG. 3 a flow diagram describing a method for reducing artifacts in an X-ray image, using an image space compensation scheme 100, is shown and discussed. In accordance with an exemplary embodiment, reconstructed image data $f_o(x, y)$ generated using an image reconstruction algorithm is obtained as shown in step 102, wherein x and y represent the spatial location within the gantry plane of gantry 2. This is preferably accomplished by operating CT imaging system 1 so as to generate raw projection data responsive to the object being scanned, wherein the raw projection data is then processed via image reconstruction device 28 using a predetermined reconstruction algorithm so as to create the reconstructed image data. Once this reconstructed image data is obtained, a noise variation characteristic for the applicable reconstruction algorithm is determined as shown in step 104. Referring to FIG. 4A and FIG. 4B, the noise variation characteristic for each algorithm may be determined theoretically or experimentally. The theoretical calculation of the noise variation characteristic $\xi(r, \phi)$ for the reconstruction algorithm under investigation over the non-weighted axial reconstruction may be calculated as follows:

$$\xi(r, \phi) = \left[ \int_{\beta_o}^{\beta_o+\Pi} w^2(\gamma, \beta-\beta_o)\sigma^2(\gamma, \beta)L^{1-4} d\beta \right]^{\frac{1}{2}} \left[ \int_{\beta_o}^{\beta_o+\Pi} \sigma^2(\gamma, \beta)L^{1-4} d\beta \right]^{-\frac{1}{2}}$$

Wherein, $(r, \phi)$ are the polar coordinate representative of $(x, y)$, $\gamma$ represents the angle of detector array 6, $\beta$ represents the ray projection angle, $\sigma(\gamma, \beta)$ is the standard deviation of the ray projection (e.g. measure projection noise) at a sample location $(\gamma, \beta)$ , P is the ray projection view range, and $L$ is the scaling factor used in the fan-beam backprojection.

Once the noise variation characteristic has been determined as shown in step 104, the reconstructed image data is filtered using so as to create smoothed image data $f_s(x, y)$ as shown in step 106, wherein x and y represent the spatial location within the gantry plane of gantry 2. The reconstructed image data is preferably filtered using a low pass filter in a manner responsive to the calculated noise variation characteristic $\xi(r,\Phi)$ as determined hereinabove. However, the reconstructed image data may be filtered in a manner responsive to the scanning technique used, the object being scanned, x-ray tube voltage and/or the x-ray tube current modulation. This is because in many CT imaging systems the x-ray tube current modulation may be used to reduce the x-ray dose exposure to the patient. Thus, the modulated x-ray current may affect and change the noise characteristics. In addition, reconstructed image data may be filtered using any filtering method or device suitable to the desired end purpose. Once the smoothed image data has been created as shown in step 106, the smoothed image data is processed using a weighting function $w(x, y)$ so as to create corrected image data $f_c(x, y)$ as shown in step 108.

Figures 4C, 5:
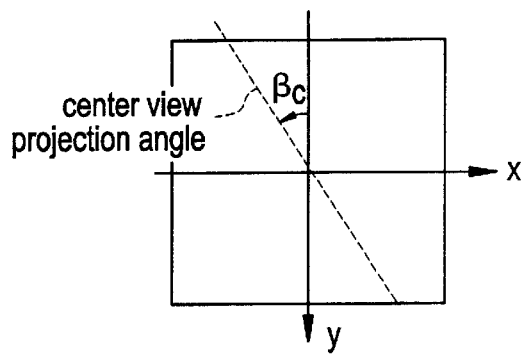
FIG. 4C is a graph of a coordinate system showing a projection angle of the center view at $-\pi/4$ formed with the vertical axis for an object scanned with high helical pitches.
FIG. 5 shows an example of a table of experimentally determined correction parameters for different scan and reconstruction modes.

Again, referring to FIG. 4A and FIG. 4B, the weighting function may be calculated as given by:

$$w(x, y) = \begin{cases} 0, & \theta(x, y) \le 0 \\ \theta(x, y), & \theta(x, y) > 0 \end{cases},$$

wherein, $\theta(x, y) = \alpha[x \sin \beta_c - y \cos \beta_c],$ $x=[(i-i_c)d]/(i_h*D),$ $y=[(j-j_c)d]/(j_h*D),$ Where, $\beta_c$ is the projection angle of the center view formed with the vertical axis for the reconstructed image, as shown in FIG. 4C. In addition, i=0,1, . . . ,511 and j=0,1, . . . ,511 are the image matrix indexes, wherein $i_c$ and $j_c$ are the iso-center location on the reconstructed image. $l_h$ and $j_h$ are the half size of the image indexes and equal 255.5. Moreover, D is the full scan field of view for the CT imaging system and d is the reconstruction field of view (field of image). Lastly, $\alpha$ is a parameter that controls the amount of correction and is responsive to the operational characteristic of CT imaging system 1. $\alpha$ may be determined via experimentation. Referring to FIG. 5, an example of experimentally determined correction parameters for different CT scan and image reconstruction modes is shown.

It should be noted that in CT, "targeted" reconstruction may be performed so as to reconstruct image data for only a specific area of the scan field of view allowing for a finer, higher resolution image. In targeted reconstruction, the entire image represents a small portion of the entire scan field of view. As such, the noise variation characteristic $\xi(r, \phi)$ is related to the weighting function for projection data and the scaling function is related to the backprojection. Ideally, these characteristics should be independent of how the reconstruction is "targeted". As such, the parameters $i_c$, $j_c$, $i_h$, $j_h$, d and D are used to remove the target reconstruction effect and convert the image pixel location to the real physical location relative to the CT system.

Moreover, the weighting function $w(x, y)$ may also vary with the object being scanned, the x-ray tube current modulation and/or x-ray tube voltage. It should be noted that in the noise variation characteristic equation hereinabove, the noise variation characteristics change with $\sigma(\gamma, \beta)$ , which is the measured projection noise. Thus, the projection noise changes with the object being scanned.

Once the weighting function has been determine as shown hereinabove, corrected image data $f_c(x, y)$ may be calculated as given by the following equation:

$f_c(x, y) = w(x, y) f_s(x, y) + [1-w(x, y)] f_o(x, y).$

Compared to the reconstructed image data $f_o(x, y)$, the corrected image data $f_c(x, y)$ have substantially more uniform noise characteristics. The corrected image data may then be stored in the data storage device for future use. Note that each corrected image data includes reconstructed 2D image data having better noise properties and although it still represents a cross-section of the scanned object, it is not 3-D image data, although 3-D images, such as MIP or VR, may be produced with the resulting corrected image data $f_c(x, y)$ using the approaches discussed previously.

Figure 6:
FIG. 6 is an example of a MIP image of a scanned object showing artifacts.
Figure 7:
FIG. 7 is an example of a MIP image of a scanned object after image correction in accordance with an exemplary embodiment.

Application of an exemplary embodiment of the method and system discussed hereinabove advantageously reconstructs image data having significantly reduced artifacts. This can be seen by referring to FIG. 6 and FIG. 7. FIG. 6 illustrates a reconstructed MIP image (acquired with a 8×1.25 mm at 13.4:1 helical pitch) prior to correction using an image space compensation scheme and exhibits a large quantity of Venetian blind artifacts. However, FIG. 7 illustrates the same reconstructed MIP image after correction using an image space compensation scheme and exhibits a large reduction in the quantity of Venetian blind artifacts (noise), in accordance with an exemplary embodiment.

This image space compensation scheme advantageously reduces the amount of artifacts present in reconstructed MIP images allowing for a sharper, clearer image. Thus, this image space compensation scheme advantageously allows imaging systems to create and reconstruct high definition 3-D MIP images while saving a great deal of time and processing power.

In accordance with an exemplary embodiment, image space compensation scheme 100 may be applied to image data obtained by any imaging system suitable to the desired end purpose, such as a magnetic resonance imaging (MRI) system.

It should be noted that the reconstructed image data may be filtered and/or the weighting function w(x, y) may be modified in a manner responsive to the presence of a pre-patient filter. For example, when different shapes of bowtie filters are used, these functions may change to adjust for the change in $\sigma(\gamma, \beta)$ In accordance with an exemplary embodiment, processing of FIG. 3 may be implemented through processing device 32 operating in response to a computer program. In order to perform the prescribed functions and desired processing, as well as the computations therefore (e.g., the execution of fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include signal input signal filtering to enable accurate sampling and conversion or acquisitions of such signals from communications interfaces. It is also considered within the scope of the invention that the processing of FIG. 3 may be implemented by a controller located remotely from processing device 32.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof.

Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for reducing artifacts in an x-ray image generated by a computed tomography imaging system using an image space compensation scheme comprising:
   obtaining reconstructed image data generated using an image reconstruction algorithm;
   determining a noise variation characteristic for said reconstruction algorithm;
   filtering said reconstructed image data so as to create smoothed image data; and
   processing said smoothed image data and said reconstructed image data so as to create corrected image data.

2. The method of claim 1, wherein said obtaining includes operating said computed tomography imaging system so as to generate raw projection data, wherein said reconstructed image data is responsive to said raw projection data.

3. The method of claim 2, wherein said obtaining includes reconstructing said raw projection data so as to create said reconstructed image data.

4. The method of claim 1, wherein said determining includes examining said reconstruction algorithm so as to identify said noise variation characteristic.

5. The method of claim 1, wherein said filtering includes filtering said reconstructed image data using a low pass filter, wherein said low pass filter is responsive to said reconstruction algorithm.

6. The method of claim 1, wherein said filtering includes filtering said reconstructed image data in a manner responsive to an applied scanning method, pre-patient filtering and an object being scanned.

7. The method of claim 1, wherein said processing includes calculating said corrected image data using a weighting function, wherein said weighting function is responsive to said noise variation characteristic.

8. The method of claim 1, wherein said processing includes calculating said corrected image data using a weighting function, wherein said weighting function is responsive to a center view projection angle.

9. The method of claim 8, wherein said center view projection angle is the projection angle of a center view formed with the image vertical axis.

10. The method of claim 1, wherein said processing includes calculating said corrected image data using a weighting function, wherein said weighting function is responsive to an applied scanning method, pre-patient filtering and an object being scanned.

11. The method of claim 1, wherein said processing includes calculating said corrected image data using a weighting function, wherein said weighting function is responsive to a correction parameter, wherein said correction parameter is determined experimentally.

12. The method of claim 1, wherein said reconstructed image data includes an image matrix having a matrix iso-center location, a mid-row index location and a mid-column index location.

13. The method of claim 12, wherein said processing includes calculating said corrected image data using a weighting function, wherein said weighting function is responsive to said matrix iso-center location, said mid-row index location, said mid-column index location, a CT imaging system full scan field of view and a reconstruction field of view.

14. A medium encoded with a machine-readable computer program code for reducing artifacts in an x-ray image generated by a computed tomography imaging system using an image space compensation scheme, said medium including instructions for causing a controller to implement a method comprising:
   obtaining reconstructed image data generated using an image reconstruction algorithm;
   determining a noise variation characteristic for said reconstruction algorithm;
   filtering said reconstructed image data so as to create smoothed image data; and
   processing said smoothed image data and said reconstructed image data so as to create corrected image data.

15. The medium of claim 14, wherein said obtaining includes operating said computed tomography imaging system so as to generate raw projection data, wherein said reconstructed image data is responsive to said raw projection data.

16. The medium of claim 15, wherein said obtaining includes reconstructing said raw projection data so as to create said reconstructed image data.

17. The medium of claim 14, wherein said determining includes examining said reconstruction algorithm so as to identify said noise variation characteristic.

18. The medium of claim 14, wherein said filtering includes filtering said reconstructed image data using a low pass filter, wherein said low pass filter is responsive to said reconstruction algorithm.

19. The medium of claim 14, wherein said filtering includes filtering said reconstructed image data in a manner responsive to an applied scanning method, pre-patient filtering and an object being scanned.

20. The medium of claim 14, wherein said processing includes calculating said corrected image data using a weighting function, wherein said weighting function is responsive to said noise variation characteristic.

21. The medium of claim 14, wherein said processing includes calculating said corrected image data using a weighting function, wherein said weighting function is responsive to a center view projection angle.

22. The medium of claim 14, wherein said processing includes calculating said corrected image data using a weighting function, wherein said weighting function is responsive to an applied scanning method, pre-patient filtering and an object being scanned.

23. The medium of claim 14, wherein said processing includes calculating said corrected image data using a weighting function, wherein said weighting function is responsive to a correction parameter, wherein said correction parameter is determined experimentally.

24. The medium of claim 14, wherein said processing includes calculating said corrected image data using a weighting function, wherein said weighting function is responsive to a CT imaging system full scan field of view, a reconstruction field of view and an image matrix having a matrix iso-center location, a mid-row index location and a mid-column index location.

25. A method for reducing artifacts in an image comprising:
   obtaining an imaging system and an object to be scanned;
   operating said imaging system so as to create projection data responsive to said object;
   examining said projection data so as to determine if said projection data should be processed; and
   processing said projection data using an image space compensation scheme wherein said compensation scheme, obtains reconstructed image data generated using an image reconstruction algorithm;
   determines a noise variation characteristic for said reconstruction algorithm;
   filters said reconstructed image data so as to create smoothed image data; and
   processes said smoothed image data and said reconstructed image data so as to create corrected image data.

26. A system for reducing artifacts in an x-ray image comprising:
   a gantry having an x-ray source and a radiation detector array, wherein said gantry defines an object cavity and wherein said x-ray source and said radiation detector array are rotatingly associated with said gantry so as to be separated by said object cavity;
   a object support structure movingly associated with said gantry so as to allow communication with said object cavity; and
   a processing device having an image space compensation scheme, wherein said compensation scheme, obtains reconstructed image data generated using an image reconstruction algorithm;
   determines a noise variation characteristic for said reconstruction algorithm;
   filters said reconstructed image data so as to create smoothed image data; and
   processes said smoothed image data and said reconstructed image data so as to create corrected image data.

27. A system for reducing artifacts in an image using an image space compensation scheme comprising:
   an imaging system;
   an object disposed so as to be communicated with said imaging system, wherein said imaging system generates projection data responsive to said object; and
   a processing device, wherein said processing device, obtains reconstructed image data generated using an image reconstruction algorithm;
   determines a noise variation characteristic for said reconstruction algorithm;
   filters said reconstructed image data so as to create smoothed image data; and
   processes said smoothed image data and said reconstructed image data so as to create corrected image data.

28. The system of claim 27, wherein said object is a patient.

29. The system of claim 27, wherein said imaging system is a computed tomography imaging system.

* * * * *